United States Patent
Gross et al.

[11] Patent Number: 5,087,295
[45] Date of Patent: Feb. 11, 1992

[54] CLEANING CYCLE FOR FLOW CYTOMETERS

[75] Inventors: Hans-Joachim Gross, Schoene Aussicht, Fed. Rep. of Germany; Robert A. Hoffman, Livermore, Calif.

[73] Assignee: Becton Dickinson and Company, Franklin Lakes, N.J.

[21] Appl. No.: 537,858

[22] Filed: Jun. 13, 1990

[51] Int. Cl.[5] .................. B08B 3/08; B08B 9/02
[52] U.S. Cl. .................... 134/26; 134/22.1; 134/22.12; 134/27; 134/28; 134/29; 252/100; 422/37
[58] Field of Search .......... 134/27, 28, 29, 22.1, 134/22.12, 26; 252/100; 422/37

[56] References Cited

U.S. PATENT DOCUMENTS

| | | | |
|---|---|---|---|
| 3,826,364 | 7/1974 | Bonner et al. | 209/3.1 |
| 4,284,412 | 8/1981 | Hansen et al. | 23/230 |
| 4,559,307 | 7/1986 | Saunders et al. | 435/34 |
| 4,607,007 | 8/1986 | Lanier et al. | 435/7 |

FOREIGN PATENT DOCUMENTS 364367 10/1988 European Pat. Off. ............. 422/37

OTHER PUBLICATIONS

Herzenberg, et al., Sci. Amer., 231:108 (1976).
McCoy, et al., A.J.C.P., 527 (Apr. 1990).

*Primary Examiner*—Theodore Morris
*Assistant Examiner*—Zeinab El Arini
*Attorney, Agent, or Firm*—Brian K. Stierwalt; Robert M. Hallenbeck

[57] ABSTRACT

A method for cleaning cellular contamination in a flow cytometer comprising the sequential use of a strong oxidizing solution, particle-free neutral pH fluid and a weak acid.

13 Claims, 4 Drawing Sheets

CLEANING CYCLE FOR FLOW CYTOMETERS

FIELD OF THE INVENTION

This invention relates to a method for cleaning a flow cytometer, and more particularly relates to an automated cleaning cycle for a flow cytometer and related peripheral equipment.

BACKGROUND OF THE INVENTION

Flow cytometry is a well accepted tool in research. It allows the user to analyze or sort tens of thousands of cells at rates of up to 10,000 cells per second. The power of this tool continues to expand and more recently applications have been designed and approved for using flow cytometers as clinical instruments in the evaluation and characterization of diseases.

An in-depth description of how a flow cytometer operates can be found in a number of references. Herzenberg et al., Sci. Amer., 231:108 (1976), describe the operation and arrangement of the prototypic instrument. Essentially, the instrument is designed to take a sample of cells and pass the cells, substantially one at a time, through a zone of illumination, wherein each cell is illuminated by a light source, typically a light source of a single wavelength such as a laser, and light scattered by each cell is collected by a series of light detectors. The results are stored in a data storage means, such as a computer, for analysis. In another form, the cells can be separated based upon their optical and other characteristics as they exit the zone of illumination in order that they may be used in further experimentation. Two examples of flow cytometers are set forth in U.S. Pat. Nos. 4,284,412 and 3,826,364.

In order to get the cells to flow through the zone of illumination substantially one at a time, the cells in the sample pass through a nozzle assembly (see e.g., 12 in FIG. 1 of U.S. Pat. No. 3,826,364) in a liquid buffer and then are coaxially fed through the zone in a particle-free sheath fluid. If the cells are to be separated, the nozzle can be vibrated at specific frequencies to cause drops to form at the tip of the nozzle wherein each drop contains a single cell.

The data collected from each cell falls into two types: scatter properties and immunofluorescent properties. In the former, each cell will scatter light from the light source based upon the size of the cell and its granularity. Scattered light can be collected by means of photodetectors which are placed at certain angles to the light source. Immunofluorescence, on the other hand, is a function of having labelled the cells with one or more immunofluorescent markers, such as a monoclonal antibody conjugated to fluorochrome. In this case, the fluorochrome(s) must be excitable by the light source and must emit at wavelengths that have peaks which do not overlap. Thus, by labelling the cells in the sample with one or more immunofluorescent markers, both scatter and immunofluorescence can be used to identify a particular cell. U.S. Pat. Nos. 4,559,307 and 4,607,007 provide two examples of how scatter and immunofluorescence can be used together to discriminate between cells in a sample.

In a typical experiment, 10,000 to 200,000 cells are analyzed. Between experiments, most manufacturers recommend that the sample buffer be introduced into the sample port and run through the instrument to clean out the entire system, including the nozzle (or flow cell). Using this method, however, it has been found that up to 0.1% of the cells in the sample remain in the system and are not washed out by routine cleaning. Generally, this does not present a problem; however, if one is looking for rare events in a sample (i.e., events that occur on the order of 1:1,000,00), then a 0.1% contamination from prior samples may lead to spurious results.

Accordingly, what is needed is a method to clean the fluidics systems of a flow cytometer which reduces the contamination in the system to essentially zero.

SUMMARY OF THE INVENTION

Figure 1A:
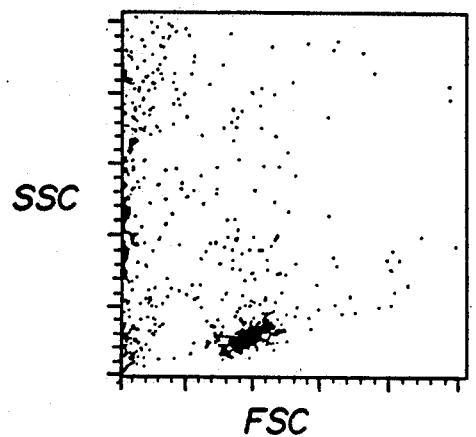
FIG. 1 comprises four dot plots of forward light scatter versus side light scatter (A), fluorescence 1 versus fluorescence 3 (B), fluorescence 2 versus fluorescence 1 (C) and fluorescence 2 versus fluorescence 3 (D) for a flow cytometer routinely maintained and cleaned in accordance with manufacturer's instructions when a particle-free solution of phosphate buffered saline is run through the flow cytometer.
Figure 1C:
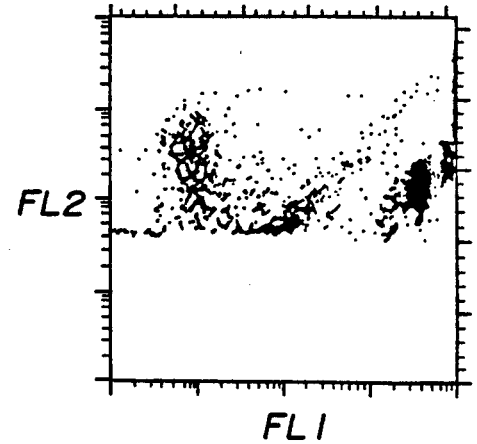
Figure 1B:
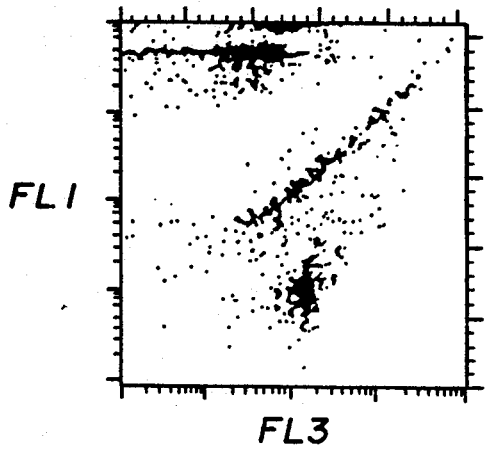
Figure 1D:
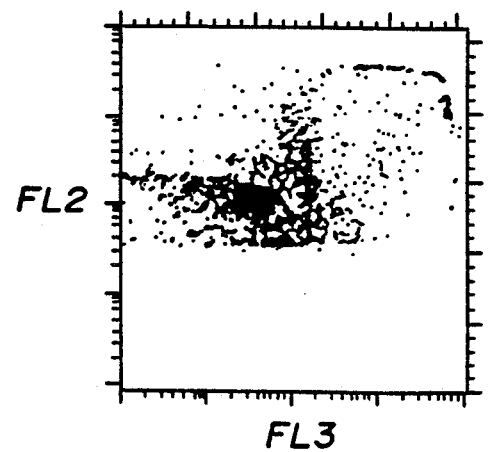
Figure 2A:
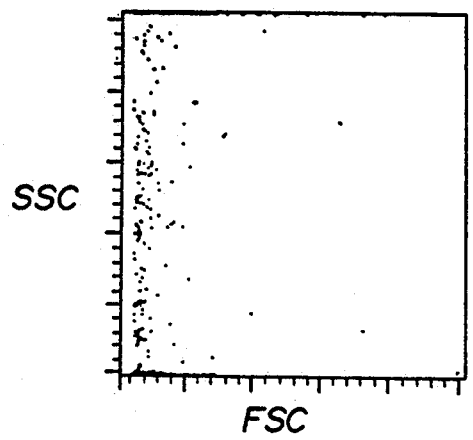
FIG. 2 comprises the same dot plots from FIG. 1 after the flow cytometer had been cleaned using the method of the invention for ungated events.
Figure 2C:
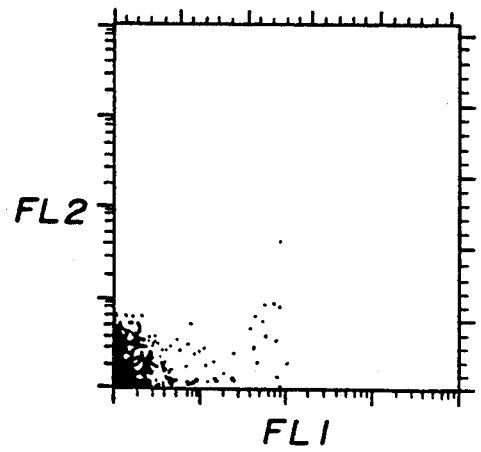
Figure 2B:
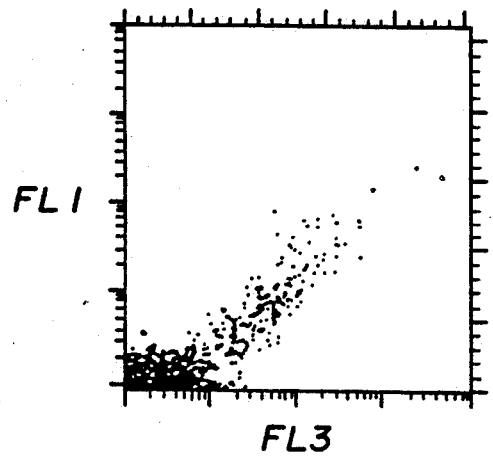
Figure 2D:
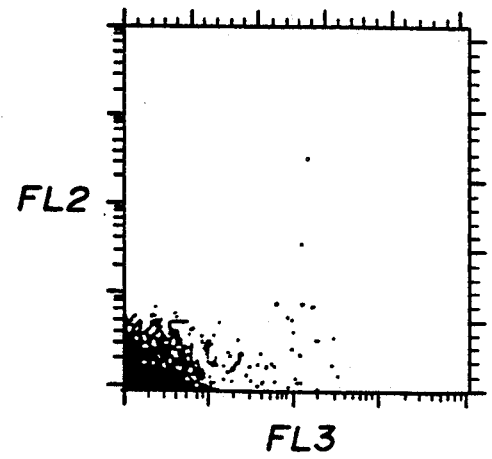
Figure 3A:
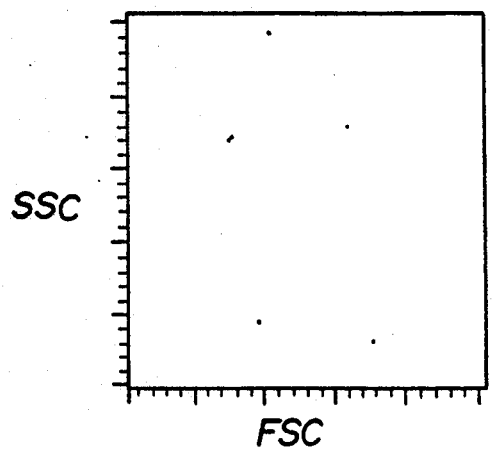
FIG. 3 comprises the same dot plots from FIG. 2 after the flow cytometer had been cleaned using the method of the invention for gated events.
Figure 3C:
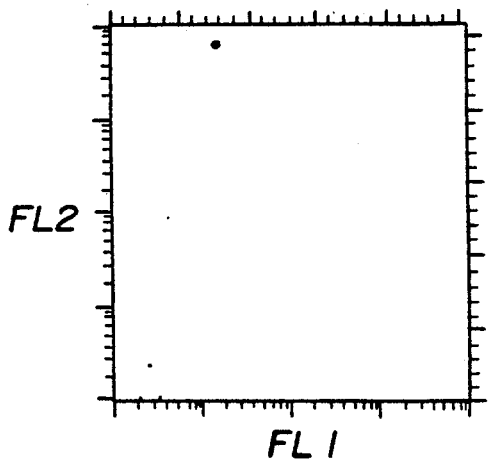
Figure 3B:
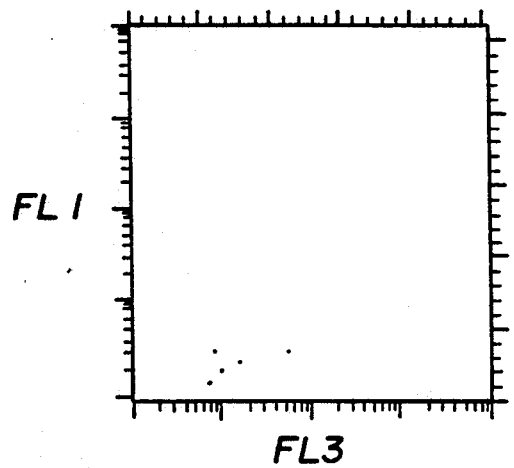
Figure 3D:
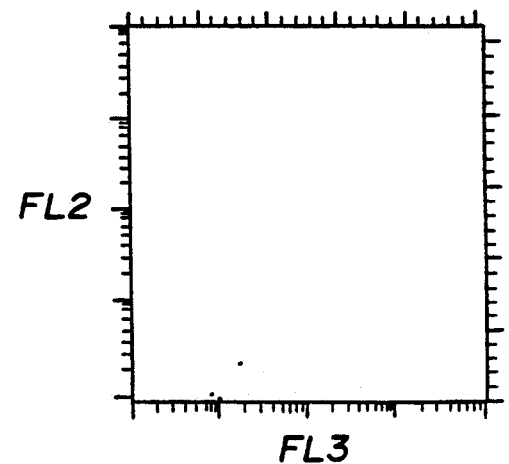

The present invention comprises a method of cleaning a flow cytometer wherein a strong oxidizing solution, a pH neutral liquid and a weak acid are sequentially run through the fluidics system of the flow cytometer. Once the system is cleaned, sheath fluid then may be used to return the flow cytometer to normal operating conditions and remove any residue of weak acid.

The invention may be carried out by introducing each of the fluids sequentially through the sample port. Alternatively, reservoirs for each of the fluids may be incorporated into the flow cytometer, and by opening and closing a series of valves, each of the fluids then may be sequentially introduced into the flow cytometer.

DETAILED DESCRIPTION OF THE INVENTION

For ease of description, the fluidics system set forth in U.S. Pat. No. 3,826,364 (FIG. 1) will be used as a model system. All reference numbers used hereinafter will refer to that patent. It will be appreciated that the practice of this invention does not depend on the specific configuration of the fluidics system, its individual components, the direction of fluid flow or on how the flow cytometer is to be used. For example, in the absence of a sample reservoir, there may simply be a sample port, such as that used on a FACScan ™ flow cytometer (Becton Dickinson Immunocytometry Systems), wherein the sample is contained in a disposable test tube which then is fitted onto the sample port for each sample to be run and then removed. The sample port then is connected to the sample feed line. In any case, how the system is configured is not as important as assuring that each component that comes in contact with the sample fluid is cleaned by the method of the invention.

The fluidics system of the flow cytometer comprises the sample fluid reservoir 14, the sample feed line 18, sheath fluid reservoir 16, sheath fluid feed line 20, pressure regulators 24 and 26 and nozzle assembly 10. The nozzle assembly 10 further comprises inner and outer coaxially located nozzles 28 and 30 which supply fluid from feeds 18 and 20 respectively. The coaxial flow stream 12 comprises an inner cell-containing portion 12A and an outer cell-free sheath fluid containing portion 12B. Receptacles to collect the cells, in the case of a cell sorter (or separator) are shown generally as 68A-C. In the case of an analyzer, where sorting is not required, there may be a waste discharge line or collection receptacle (not shown).

To clean the flow cytometer, a strong oxidizing solution is added to reservoirs 14 and 16. Strong oxidizing solutions useful in the practice of this invention should have an oxidizing potential of greater than 0.7 V. Examples of such solutions include a mixture of NaOH and NaOCl and a mixture of KOH and KOCl. The mixture of NaOH and NaOCl is preferred. Without applying any pressure through the regulators 24 and 26, the solution is allowed to flood the entire fluidics system. It is left in the system for between 10 seconds to 10 minutes with 30 seconds being optimal.

After this time period, the sample reservoir 14 is drained through the system and air is introduced through the sample reservoir 14. As air is introduced, the oxidizing solution is run through the sheath reservoir 16 under pressure until empty. The reservoirs then are filled with a neutral pH fluid. This fluid must be particle free. Preferredly, the fluid is deionized water. A preservative, such as sodium azide, may be added to the fluid. The purpose of the preservative is to prevent microorganism growth. The fluidics system then is run under pressure with the neutral pH fluid until empty.

The reservoirs 14 and 16 then are filled with a weak acid having a $P_k$ value of approximately 3. Weak acids useful in the practice of this invention include 0.01M acetic acid and 0.01M N-tri-chloroacetic acid. Acetic acid is preferred. Again, the fluidics system is run under pressure until the reservoirs are empty.

Finally, sheath fluid is re-filled into the sheath fluid reservoir 16 and run under pressure for approximately 2 minutes to wash away any remaining acid. The fluidics system now will be essentially free of cells that could contaminate a sample.

Figure 4:
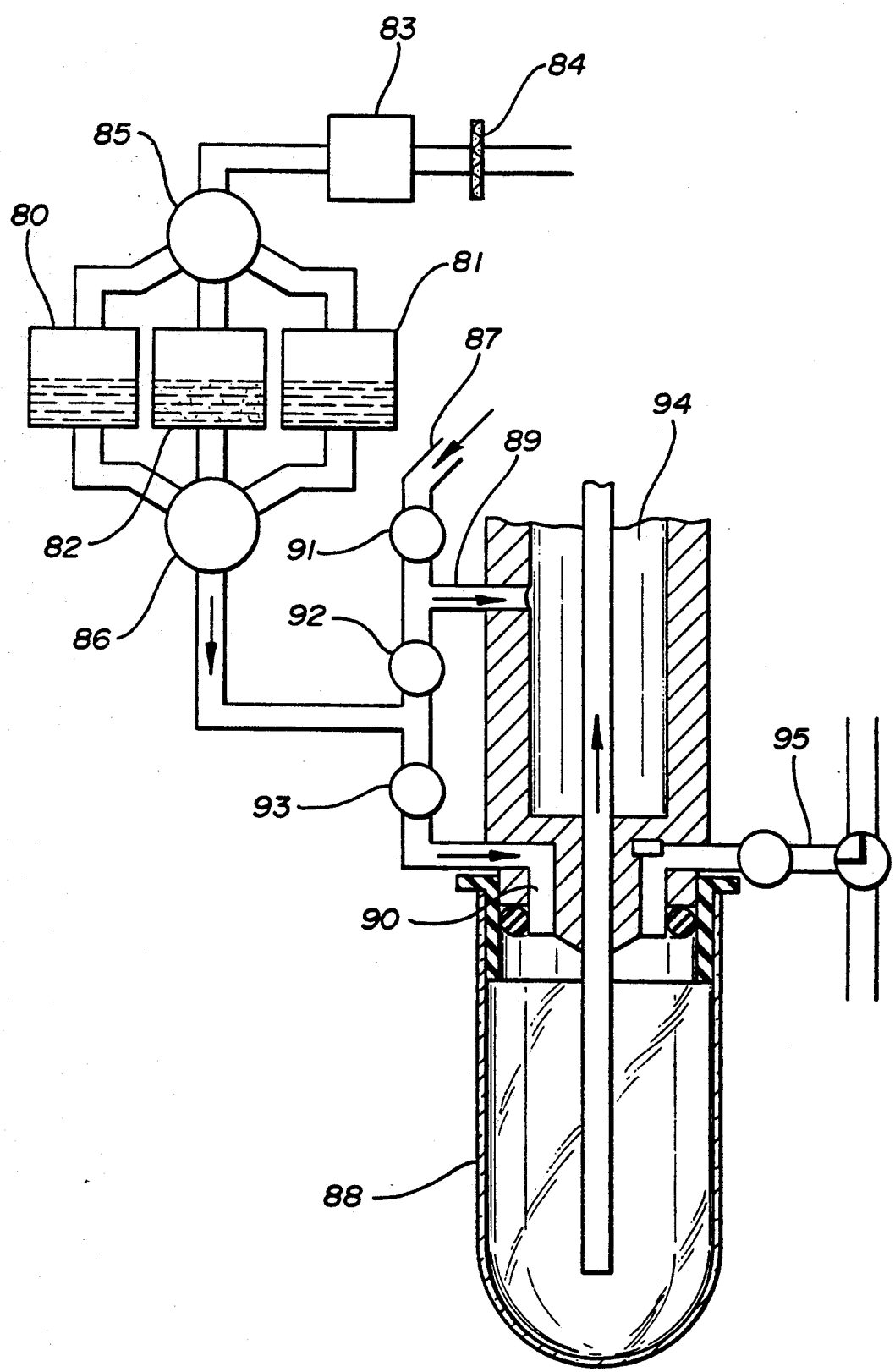
FIG. 4 comprises a schematic drawing of one embodiment of a flow cytometer fluidics system equipped to clean the system in accordance with the claimed invention.

In another embodiment of this system, three reservoirs may be added to the fluidics system. See, e.g., FIG. 4. One reservoir 80 will contain the strong oxidizing solution, one 81 will contain the neutral pH fluid and the other 82 will contain the weak acid. Air to pressurize the reservoirs is provided by a pump 83 which is in line with a filter 84. A rotary valve 85 is provided to direct the flow of air to each of the reservoirs. The reservoirs will be connected to the fluidics system at a point where cells first come in contact with the system (e.g., sample port 88) by means of a common feed metered through another rotary valve 86. In the embodiment shown, the common feed connects in with the sheath fluid inlet 87. This inlet has two points of entry: one into the flow cell 89 and the other 90 into the sample port 88. The flow of sheath fluid is controlled by pinch valves 9-1, 92 and 93. The sample injection tube from the sample port 88 to the flow cell (not shown) is shown generally as 94. An additional metered air supply to pressurize the sample port is shown generally as 95.

In another embodiment, a sample preparation station, such as FACSPrep TM (BDIS), which provides for programmable staining of samples followed by introduction of the samples into the flow cytometer also can be modified to be cleaned in accordance with the invention. In this embodiment the reservoir system described above can incorporated into the preparation station alone or in combination with a system in the flow cytometer.

To demonstrate the effectiveness of this method, a FACScan TM flow cytometer which had been used to run a variety of cell samples was cleaned in accordance with the manufacturer's directions (e.g., by running a solution of household bleach through the fluidics system and then flushing with sheath fluid). Phosphate buffered saline (free of any particles) then was run through the flow cytometer as a "sample." Two measurements of scatter were recorded and three measures of fluorescence were recorded (ungated). The results are set forth in FIG. 1. As can be seen, significant background levels of scatter and fluorescence were detected using conventional cleaning methods.

In accordance with the invention, a strong oxidizing solution consisting of a mixture of 0.05M NaOH and 0.07M NaOCl, particle-free deionized water, and 0.01M acetic acid were run through the flow cytometer sequentially. PBS then was run through the flow cytometer as a "sample." Again, two measures of scatter and three measures of fluorescence were recorded. As can be seen from FIGS. 2 and 3, after 9 hours of the PBS "sample" only six events were recorded by scatter and none by fluorescence within the gate. Contamination of the fluidics system of the flow cytometer, therefore, was reduced essentially to zero.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

We claim:

1. A method for cleaning a flow cytometer comprising adding sequentially to the fluidics system a strong oxidizing solution, a particle-free neutral pH fluid and a weak acid wherein the weak acid has a value of approximately 3.

2. The method of claim 1 wherein the strong oxidizing solution has an oxidizing value of greater than 0.7 V.

3. The method of claim 2 wherein the strong oxidizing solution is selected from the group consisting of a mixture of NaOH and NaOCl and a mixture of KOH and KOCl.

4. The method of claim 3 wherein the strong oxidizing solution is a mixture of NaOH and NaOCl.

5. The method of claim 1 wherein the neutral pH fluid is deionized water.

6. The method of claim 5 wherein a preservative is added to the fluid.

7. The method of claim 6 wherein the preservative is sodium azide.

8. The method of claim 1 wherein the weak acid is selected from the group consisting of acetic acid and N-tri-chloroacetic acid.

9. The method of claim 8 wherein the weak acid is acetic acid.

10. The method of claim 1 wherein the fluidics system is equilibrated with a sheath fluid as a last step.

11. A method for cleaning a flow cytometer of cellular contamination which comprises the sequential steps of adding to the fluidics system a mixture of NaOH and NaOCl for several minutes, flushing the system with air and the mixture of NaOH NaOCl as a sheath fluid, flushing the system with particle-free deionized water containing sodium azide, flushing the system with acetic acid and equilibrating the system with a sheath fluid.

12. The method of claim 11 wherein the mixture comprises 0.05M NaOH and 0.07M NaOCl.

13. The method of claim 11 wherein the acetic acid is 0.01M.

* * * * *